US008323709B2

(12) United States Patent
Omelchenko

(10) Patent No.: US 8,323,709 B2
(45) Date of Patent: Dec. 4, 2012

(54) EDIBLE SPOON FOR DISSOCIATING INTO CONSUMABLE PREDETERMINED CLUMPS IN ORDER TO PREVENT DISSOCIATING INTO RANDOM GRANULES THAT WOULD MAKE CONSUMPTION MORE DIFFICULT

(76) Inventor: Anatoliy Omelchenko, Brooklyn, NY (US)

( * ) Notice: Subject to any disclaimer, the term of this patent is extended or adjusted under 35 U.S.C. 154(b) by 408 days.

(21) Appl. No.: 12/798,821

(22) Filed: Apr. 12, 2010

(65) Prior Publication Data

US 2011/0091521 A1    Apr. 21, 2011

Related U.S. Application Data

(60) Provisional application No. 61/279,225, filed on Oct. 19, 2009.

(51) Int. Cl.
*A21D 13/00* (2006.01)
(52) U.S. Cl. .......... 426/76; 426/104; 426/144; 426/549; D1/121; D1/122; D1/123; D1/124; D1/128
(58) Field of Classification Search .............. 426/76, 426/104, 138–139, 144, 549; D1/121–124, D1/128
See application file for complete search history.

(56) References Cited

U.S. PATENT DOCUMENTS

| | | | | |
|---|---|---|---|---|
| 1,509,194 A | * | 9/1924 | Dresser | 426/76 |
| D193,541 S | * | 9/1962 | Gordon | D1/123 |
| D193,542 S | * | 9/1962 | Gordon | D1/123 |
| D195,498 S | | 6/1963 | Gordon | D8/1 |
| D212,070 S | * | 8/1968 | Hreschak | D1/123 |
| D213,946 S | | 4/1969 | Cooper et al. | D1/2 |
| D219,003 S | * | 10/1970 | Harwood | D1/123 |
| 3,840,678 A | * | 10/1974 | Price | 426/104 |
| 4,205,091 A | * | 5/1980 | Van Horne | 426/138 |
| 4,606,923 A | * | 8/1986 | Ricke | 426/496 |
| D338,993 S | | 9/1993 | Lilly | D1/106 |
| D339,218 S | | 9/1993 | Welsh et al. | D1/106 |
| D354,613 S | * | 1/1995 | Kreger | D1/124 |
| D564,726 S | * | 3/2008 | Bortkiewicz | D1/121 |
| D586,535 S | * | 2/2009 | Soliz | D1/123 |
| D632,046 S | * | 2/2011 | Omelchenko | D1/106 |
| 2001/0043968 A1 | * | 11/2001 | Rhee | 426/76 |

(Continued)

FOREIGN PATENT DOCUMENTS

CN        87202651 U    1/1988

(Continued)

OTHER PUBLICATIONS

Patent Cooperation Treaty PCT Notification of Transmittal of the International Search Report and the Written Opinion of the International Searching Authority (1-2 pages), date:2011.

(Continued)

*Primary Examiner* — Drew Becker
*Assistant Examiner* — Luana Z Long
(74) *Attorney, Agent, or Firm* — Bernard S. Hoffman

(57) ABSTRACT

An edible spoon for dissociating into consumable predetermined clumps in order to prevent dissociating into random granules that would make consumption more difficult. The edible spoon includes a bowl and a handle. The bowl extends from the handle and contains weakened lines. The weakened lines in the bowl define the consumable predetermined clumps so as to allow the bowl to dissociate into the consumable predetermined clumps in order to prevent dissociating into the random granules that would make the consumption more difficult.

9 Claims, 4 Drawing Sheets

U.S. PATENT DOCUMENTS

2005/0089604 A1* 4/2005 Pastore .................. 426/101
2007/0292566 A1 12/2007 DeGennaro ................ 426/104

FOREIGN PATENT DOCUMENTS

| FR | 2797747 A | 3/2001 |
|----|-----------|--------|
| JP | 61-037056 A | 2/1986 |
| JP | 61037056 A | 2/1986 |
| JP | 3142376 I9 | 5/2008 |
| KR | 20-1998-0011661 U | 5/1998 |
| WO | WO01/06900 A1 | 2/2001 |

OTHER PUBLICATIONS

Patent Cooperation Treat PCT International Search Report (1-3 pages).

Patent Cooperation Treaty PCT Written Opinion of the International Searching Authority (1-3 pages), date:2011.

* cited by examiner

EDIBLE SPOON FOR DISSOCIATING INTO CONSUMABLE PREDETERMINED CLUMPS IN ORDER TO PREVENT DISSOCIATING INTO RANDOM GRANULES THAT WOULD MAKE CONSUMPTION MORE DIFFICULT

1. CROSS REFERENCE TO RELATED APPLICATIONS

The instant non-provisional patent application claims priority from provisional patent application No. 61/279,225, filed on Oct. 19, 2009, for an ECO-FRIENDLY SPOON, and incorporated herein by reference thereto.

2. BACKGROUND OF THE INVENTION

A. Field of the Invention

The embodiments of the present invention relate to a spoon, and more particularly, the embodiments of the present invention relate to an edible spoon for dissociating into consumable predetermined clumps in order to prevent dissociating into random granules that would make consumption more difficult.

B. Description of the Prior Art

Numerous innovations for spoons have been provided in the prior art, which will be described below in chronological order to show advancement in the art, and which are incorporated herein by reference thereto. Even though these innovations may be suitable for the specific individual purposes to which they address, however, they differ from the embodiments of the present invention in that they do not teach an edible spoon for dissociating into consumable predetermined clumps in order to prevent dissociating into random granules that would make consumption more difficult.

(1) U.S. Pat. No. Des. 195,498 to Gordon.

U.S. Pat. No. Des. 195,498 issued, to Gordon on Jun. 25, 1963 in U.S. class D8 and subclass 1 teaches the ornamental design for an edible serving spoon.

(2) U.S. Pat. No. Des. 213,946 to Cooper et al.

U.S. Pat. No. Des. 213,946 issued to Cooper et al. on Apr. 29, 1969 in U.S. class D1 and subclass 2 teaches the ornamental design for a snack food product or the like.

(3) Japanese Patent Application Publication Number JP61037056 (A) to Suzuko.

Japanese Patent Application Publication Number JP61037056 (A) published to Suzuko on Feb. 21, 1986 in international class A47G21 and subclass 04 teaches a tilted spoon manufactured by forming an edible material, such as wheat flour, in the form of a tea spoon. A drink, such as coffee, can be taken while eating the tea spoon.

(4) Patent Application Publication Number CN87202651 (U) to Laili.

Patent Application Publication Number CN87202651 (U) published to Laili on Jan. 13, 1988 in international class A47G21 and subclass 04 teaches a dual-purpose spoon used for taking meals and medicine, which is suitable for children to use in taking meals and medicine. The spoon is made by connecting a funnel at the back of an ordinary spoon, and the tail of the funnel is appropriately extended into a straw. The spoon can be used as an ordinary spoon in having meals. For the use in taking medicine, physic liquor can be held in the spoon part, and the straw is inserted into the mouth of the child to achieve the purpose of feeding medicine.

(5) U.S. Pat. No. Des. 338,993 to Lilly.

U.S. Pat. No. Des. 338,993 issued to Lilly on Sep. 7, 1993 in U.S. class D1 and subclass 106 teaches the ornamental design for an edible spoon.

(6) U.S. Pat. No. Des. 339,218 to Welsh et al.

U.S. Pat. No. Des. 339,218 issued to Welsh et al. on Sep. 14, 1993 in U.S. class D1 and subclass 106 teaches the ornamental design for an edible spoon.

(7) International Patent Application Publication Number WO 01/06900 A1 to Eliasen et al.

International Patent Application Publication Number WO 01/06900 A1 published to Eliasen et al. on Feb. 1, 2001 in international class A47G21 and subclass 18 teaches an edible straw, a dinner knife as a straw, a dinner fork as a straw, a dinner spoon as a straw, and a straw in all kinds of colors and shapes, made of bonbons, sugar, or other kinds of candy. The edible straw, the dinner knife as a straw, the dinner fork as a straw, the dinner spoon as a straw, and the straw have a hole in both ends making it possible to use it as cutlery and a straw, and at the same time is edible.

(8) French Patent Application Publication Number FR2797747 (A1) to Dubreuil.

French Patent Application Publication Number FR2797747 (A1) published to Dubreuil on Mar. 2, 2001 in international class A21D13 and subclass 08 teaches a spoon or spatula agitator composed of a long consumable body on which a widened agitating head is fastened. The edible materials including the head include a chocolate based material.

(9) United States Patent application Publication Number US 2007/0292566 A1 to DeGennaro.

United States Patent Application Publication Number US 2007/0292566 A1 published to DeGennaro on Dec. 20, 2007 in U.S. class 426 and subclass 104 teaches a lollipop with a conventional stem or handle, and an edible part in the shape of a spoon for administering liquid medications. The lollipop is used to administer liquid medications to children, developmentally challenged adults, or adults who dislike the taste of liquid medications. The lollipop spoons can be packaged for sale individually as a package or together with containers of liquid medications.

It is apparent that numerous innovations for spoons have been provided in the prior art, which are adapted to be used. Furthermore, even though these innovations may be suitable for the specific individual purposes to which they address, however, they would not be suitable for the purposes of the embodiments of the present invention as heretofore described, namely, an edible spoon for dissociating into consumable predetermined clumps in order to prevent dissociating into random granules that would make consumption more difficult.

3. SUMMARY OF THE INVENTION

Thus, it is an object of the embodiments of the present invention to provide an edible spoon for dissociating into consumable predetermined clumps in order to prevent dissociating into random granules that would make consumption more difficult, which avoids the disadvantages of the prior art.

Briefly stated, another object of the embodiments of the present invention is to provide an edible spoon for dissociating into consumable predetermined clumps in order to prevent dissociating into random granules that would make consumption more difficult. The edible spoon includes a bowl and a handle. The bowl extends from the handle and contains weakened lines. The weakened lines in the bowl define the consumable predetermined clumps so as to allow the bowl to dissociate into the consumable predetermined clumps in order to prevent dissociating into the random granules that would make the consumption more difficult.

The novel features considered characteristic of the embodiments of the present invention are set forth in the appended claims. The embodiments of the present invention themselves, however, both as to their construction and to their method of operation together with additional objects and advantages thereof will be best understood from the following description of the specific embodiments when read and understood in connection with the accompanying drawings.

4. BRIEF DESCRIPTION OF THE DRAWINGS

The figures of the drawings are briefly described as follows.

5. LIST OF REFERENCE NUMERALS UTILIZED IN THE DRAWINGS

Figure 1:
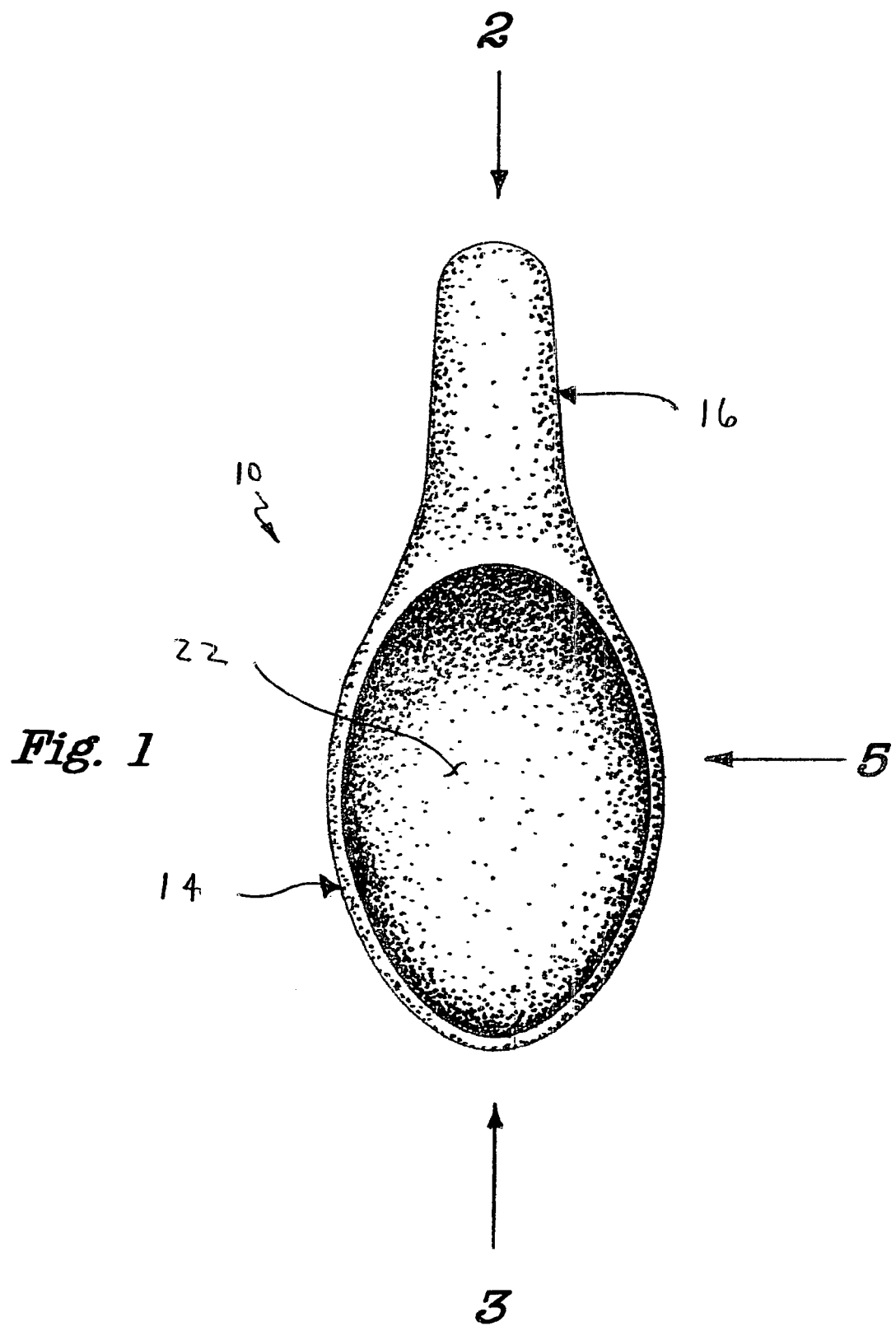
FIG. 1 is a diagrammatic top plan view of the edible spoon of the embodiments of the present invention for dissociating into consumable predetermined clumps in order to prevent dissociating into random granules that would make consumption more difficult.

A. General.
10 edible spoon of embodiments of present invention for dissociating into consumable predetermined clumps 12 in order to prevent dissociating into random granules that would make consumption more difficult
12 consumable predetermined clumps
B. Configuration of Edible Spoon 10.
14 bowl
16 handle
18 weakened lines in bowl 14
20 matrix of indents of weakened lines 18 in bowl 14
22 top surface of bowl 14
24 bottom surface of bowl 14
26 at least one axial indent of matrix of indents 20 of weakened lines 18 in bowl 14
28 at least one lateral indent of matrix of indents 20 of weakened lines 18 in bowl 14

6. DETAILED DESCRIPTION OF THE PREFERRED EMBODIMENTS

A. General.

Figure 2:
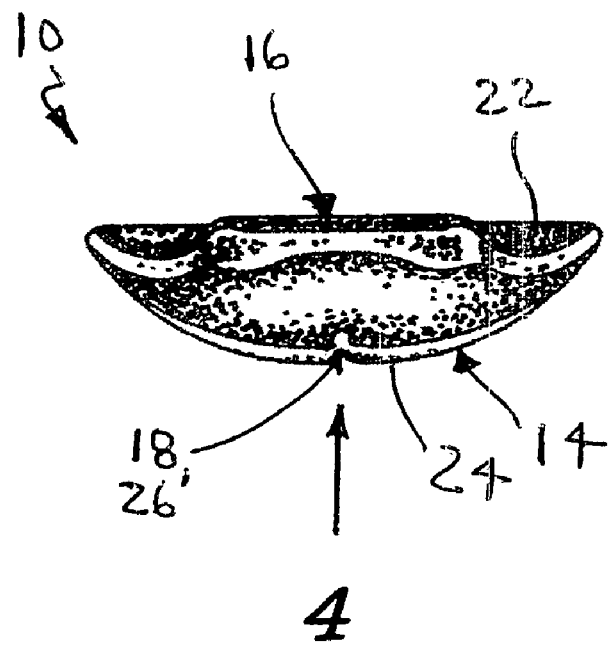
FIG. 2 is a diagrammatic rear end view taken in the direction of ARROW 2 in FIG. 1.
Figure 3:
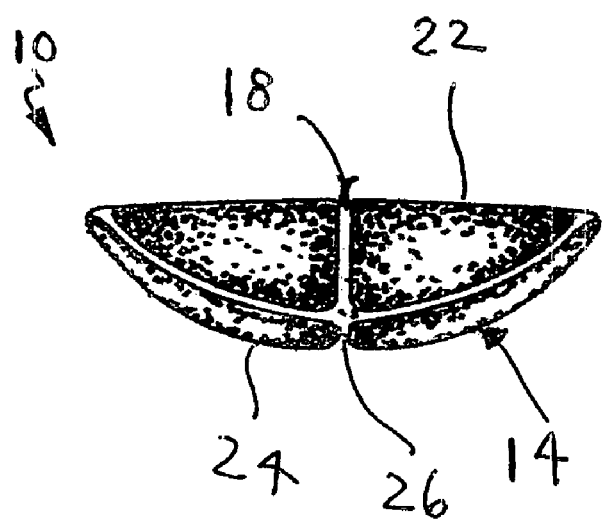
FIG. 3 is a diagrammatic front end view taken in the direction of ARROW 3 in FIG. 1.

Referring now to the drawings, in which like numerals indicate like parts, and particularly to FIGS. 1-5, which are, respectively, a diagrammatic top plan view of the edible spoon of the embodiments of the present invention for dissociating into consumable predetermined clumps in order to prevent dissociating into random granules that would make consumption more difficult, a diagrammatic rear end view taken in the direction of ARROW 2 in FIG. 1, a diagrammatic front end view taken in the direction of ARROW 3 in FIG. 1, a diagrammatic bottom plan view taken in the direction of ARROW 4 in FIG. 2, and a diagrammatic side elevational view taken in the direction of ARROW 5 in FIG. 1, the edible spoon of the embodiments of the present invention is shown generally 10 for dissociating into consumable predetermined clumps 12 (FIG. 4) in order to prevent dissociating into random granules that would make consumption more difficult.

B. The Configuration of the Edible Spoon 10.

The edible spoon 10 includes a bowl 14 and a handle 16. The bowl 14 extends from the handle 16 and contains weakened lines 18. The weakened lines 18 in the bowl 14 define the consumable predetermined clumps 12 so as to allow the bowl 14 to dissociate into the consumable predetermined clumps 12 in order to prevent dissociating into the random granules that would make the consumption more difficult.

The bowl 14 is dissociated into the consumable predetermined clumps 12 by, preferably, biting off a consumable predetermined clump 12, snapping off a consumable predetermined clump 12, etc., after the edible spoon 10 has been utilized for its intended purpose, and as such, the edible spoon 10 is, preferably, made from corn flour, wheat flour, salt, and water, and, secondarily, chili pepper and sugar, and when mixed, are substantially resistant to deformation and disintegration due to contact with a drinkable liquid or an edible food for an acceptable period of time.

The edible spoon 10 contains an edible selected from the group consisting of a desert food, vitamin(s), medication(s), breath mint(s), hard candy, candy, chocolate, etc., and combinations thereof that are substantially resistant to deformation and disintegration due to contact with a drinkable liquid or an edible food for an acceptable period of time.

Figure 4:
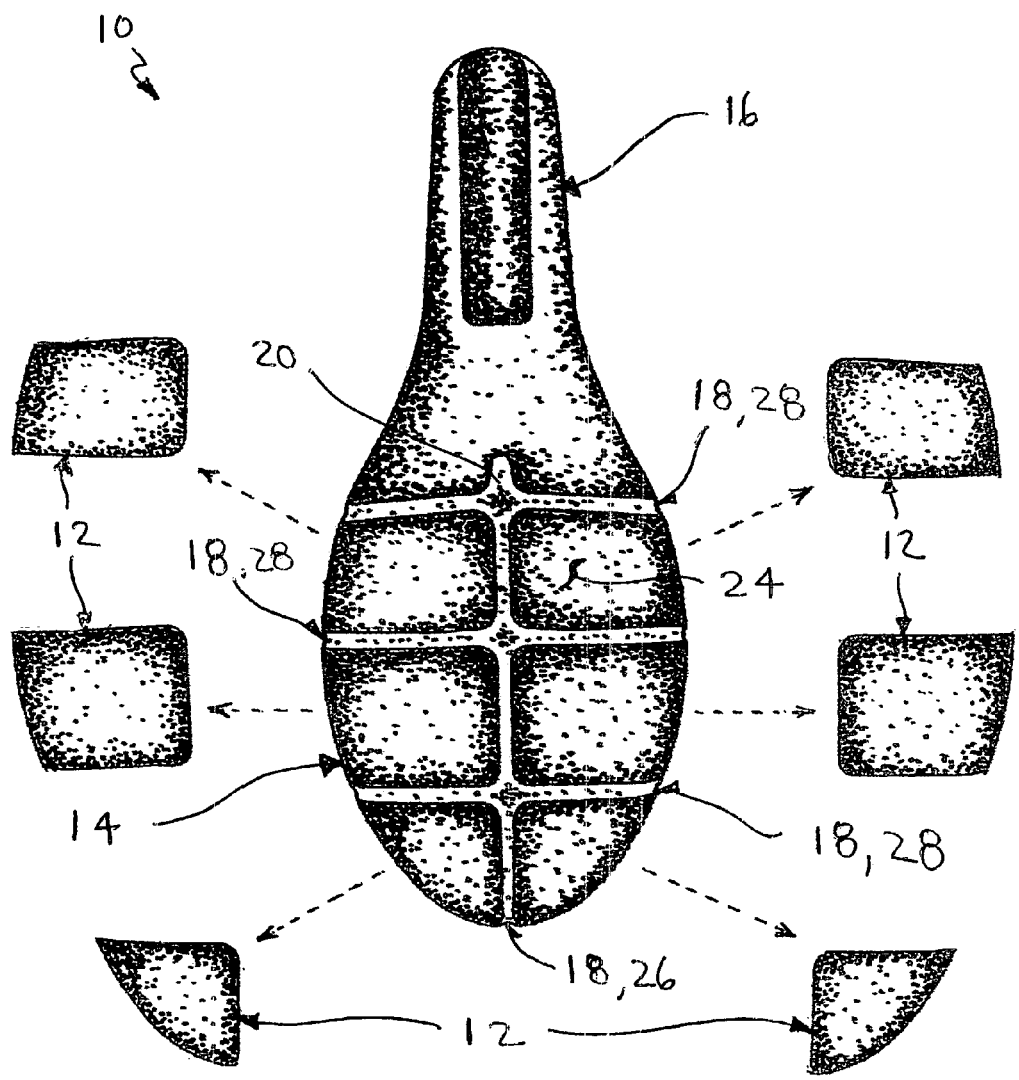
FIG. 4 is a diagrammatic bottom plan view taken in the direction of ARROW 4 in FIG. 2.
Figure 5:
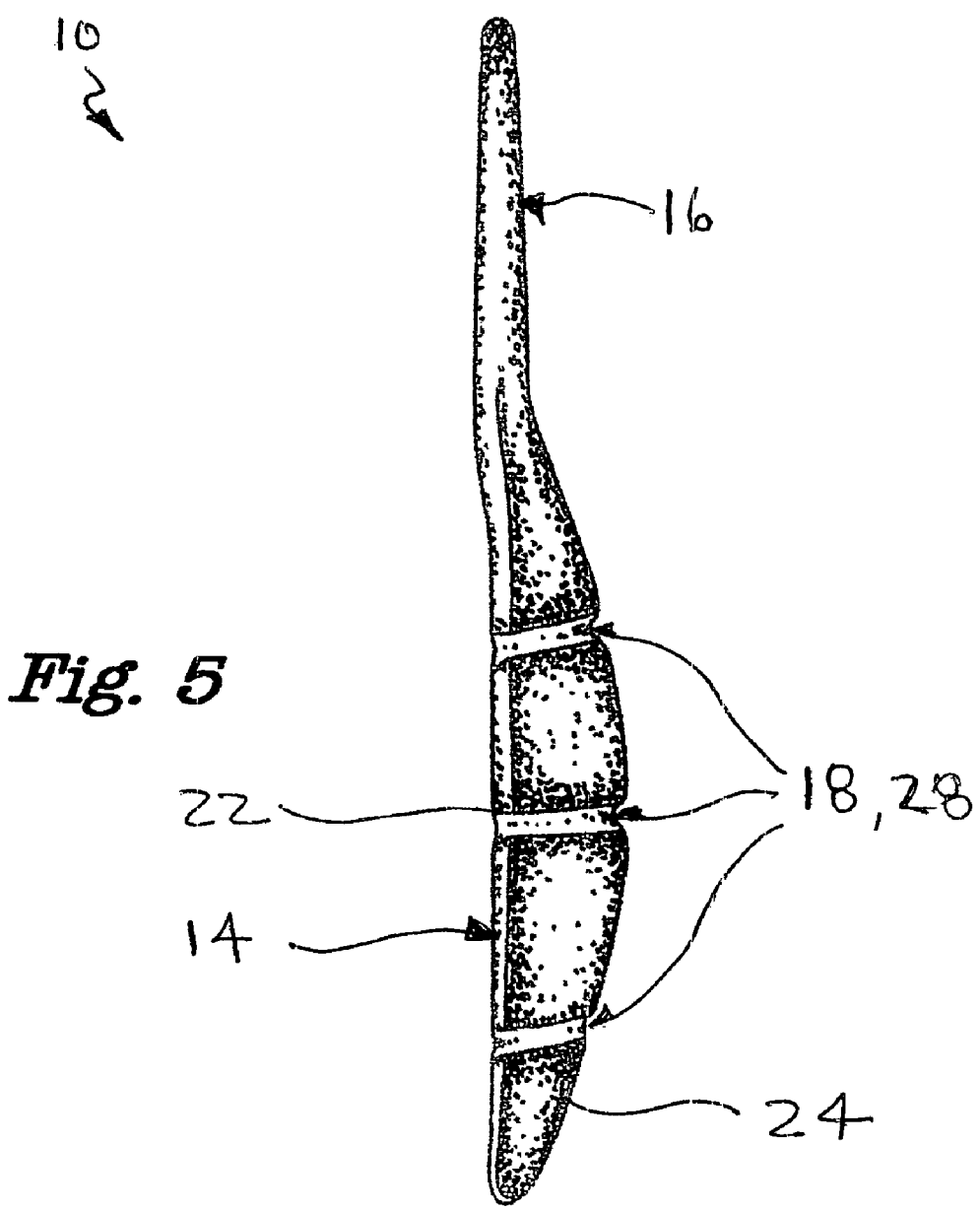
FIG. 5 is a diagrammatic side elevational view taken in the direction of ARROW 5 in FIG. 1.

The weakened lines 18 of the bowl 14 form a matrix of indents 20 (FIG. 4).

The bowl 14 has a top surface 22, a bottom surface 24, and a size. The weakened lines 18 of the bowl 14 are disposed on the bottom surface 24 of the bowl 14 so as not to provide voids in which food in the bowl 14 can be trapped.

The matrix of indents 20 in the bowl 14, preferably, contains at least one axial indent 26 with an orientation and a shape, and at least one lateral indent 28 with an orientation and a shape. The at least one lateral indent 28 in the bowl 14 crosses the at least one axial indent 26 in the bowl 14. The at least one axial indent 26 in the bowl 14 and the at least one lateral indent 28 in the bowl 14 depend in number, orientation, and shape on the size of the bowl 14.

C. Impression.

It will be understood that each of the elements described above or two or more together may also find a useful application in other types of constructions differing from the types described above.

While the embodiments of the present invention have been illustrated and described as embodied in an edible spoon for dissociating into consumable predetermined clumps in order to prevent dissociating into random granules that would make consumption more difficult, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis, the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. An edible spoon for dissociating into consumable predetermined clumps in order to prevent dissociating into random granules that would make consumption more difficult, comprising:

a) a bowl; and b) a handle;

wherein said bowl extends from said handle;
wherein said bowl contains weakened lines; and
wherein said weakened lines in said bowl define said consumable predetermined clumps so as to allow said bowl to dissociate into said consumable predetermined clumps in order to prevent dissociating into the random granules that would make the consumption more difficult.

2. The spoon of claim 1, wherein said weakened lines in said bowl form a matrix of indents.

3. The spoon of claim 1, wherein said bowl has a bottom surface; and
wherein said weakened lines in said bowl are disposed on said bottom surface of said bowl so as not to provide voids in which food in said bowl can be trapped.

4. The spoon of claim 2, wherein said matrix of indents in said bowl contains at least one axial indent; and
wherein said matrix of indents in said bowl contains at least one lateral indent.

5. The spoon of claim 4, wherein said at least one lateral indent of said matrix of indents in said bowl crosses said at least one axial indent in said matrix of indents in said bowl.

6. The spoon of claim 4, wherein said bowl has a size; and
wherein said at least one axial indent of said matrix of indents in said bowl and said at least one lateral indent of said matrix of indents in said bowl depend in number, orientation, and shape on said size of said bowl.

7. The spoon of claim 1, wherein said edible spoon is made from corn flour, wheat flour, salt, and water, and when mixed, are substantially resistant to deformation and disintegration due to contact with a drinkable liquid or an edible food for an acceptable period of time.

8. The spoon of claim 7, wherein said edible spoon is further made from chili pepper and sugar, and when mixed, are substantially resistant to deformation and disintegration due to contact with a drinkable liquid or an edible food for an acceptable period of time.

9. The spoon of claim 1, wherein said edible spoon contains an edible selected from the group consisting of a desert food, vitamins, medications, breath mints, hard candy, candy, and chocolate, which are substantially resistant to deformation and disintegration due to contact with a drinkable liquid or an edible food for an acceptable period of time.

* * * * *